United States Patent [19]

Lohrmann et al.

[11] Patent Number: 5,716,597
[45] Date of Patent: Feb. 10, 1998

[54] EMULSIONS AS CONTRAST AGENTS AND METHOD OF USE

[75] Inventors: Rolf Lohrmann, La Jolla; Kenneth J. Widder, Rancho Santa Fe; Ashwin M. Krishnan, San Diego; Dung Kevin Hong, San Diego; Jialun Meng, San Diego, all of Calif.

[73] Assignee: Molecular Biosystems, Inc., San Diego, Calif.

[21] Appl. No.: 72,535

[22] Filed: Jun. 4, 1993

[51] Int. Cl.⁶ .............................. A61K 49/00; B01J 13/00
[52] U.S. Cl. .......................... 424/9.5; 252/312; 424/450; 128/662.02
[58] Field of Search ...................... 252/312; 424/9, 424/450; 128/662.02, 9.52

[56] References Cited

U.S. PATENT DOCUMENTS

| | | | |
|---|---|---|---|
| 3,778,381 | 12/1973 | Rosano et al. | 252/312 |
| 4,276,885 | 7/1981 | Tickner et al. | 128/662.02 |
| 4,466,442 | 8/1984 | Hilmann et al. | 128/662.02 |
| 4,572,203 | 2/1986 | Feinstein | 128/662.02 |
| 4,622,219 | 11/1986 | Haynes | 424/450 |
| 4,718,433 | 1/1988 | Feinstein | 128/662.02 |
| 4,725,442 | 2/1988 | Haynes | 424/450 |
| 4,774,958 | 10/1988 | Feinstein | 128/660.01 |
| 4,844,882 | 7/1989 | Widder et al. | 424/9.5 |
| 4,900,540 | 2/1990 | Ryan et al. | 424/9 |
| 4,957,656 | 9/1990 | Cerny et al. | 252/311 |
| 4,996,041 | 2/1991 | Arai et al. | 424/9 |
| 5,088,499 | 2/1992 | Unger | 128/662.02 |
| 5,123,414 | 6/1992 | Unger | 424/450 |
| 5,137,928 | 8/1992 | Erbel et al. | 521/56 |
| 5,147,631 | 9/1992 | Glajch et al. | 424/9.5 |
| 5,234,680 | 8/1993 | Rogers, Jr. et al. | 424/9 |
| 5,271,928 | 12/1993 | Schneider et al. | 424/9 |
| 5,393,524 | 2/1995 | Quay | 424/9 |
| 5,409,688 | 4/1995 | Quay | 424/9 |
| 5,558,855 | 9/1996 | Quay | 424/9.5 |

FOREIGN PATENT DOCUMENTS

| | | |
|---|---|---|
| 0327490 | 8/1989 | European Pat. Off. . |
| 0357163 | 6/1992 | European Pat. Off. . |
| WO 92/05806 | 4/1992 | WIPO . |
| WO92/15284 | 9/1992 | WIPO . |
| WO 92/17212 | 10/1992 | WIPO . |
| WO 92/17213 | 10/1992 | WIPO . |
| WO 93/05819 | 4/1993 | WIPO . |
| WO 94/06477 | 3/1994 | WIPO . |
| WO 94/16739 | 8/1994 | WIPO . |

OTHER PUBLICATIONS

Ophir et al., "Contrast agents in diagnostic ultrasound" *Ultrasound in Med & Biol.* (1989) 15(4):319–333.

Carroll et al., "Gelatin encapsulated nitrogen microbubbles as ultrasound contrast agents" *Investigative Radiology* (1980) 15(3):260–266.

Carroll et al., "Ultrasonic contrast enhancement of tissue by encapsulated microbubbles" *Ultrasound* (1982) 143(3):747–750.

Grinstaff et al., "Air–filled proteinaceous microbubbles: synthesis of an echo–contrast agents" *Proc. Natl. Acad. Sci. USA* (1991) 88:7708–7710.

Meltzer et al., "Why do the lungs clear ultrasound contrast?" *Ultrasound in Med. & Biol.* (1980) 6:263–269.

Suslick et al., "Protein microencapsulation of nonaqueous liquids" *J. Am. Chem. Soc.* (1990) 112:1807–1809.

*Primary Examiner*—Richard D. Lovering
*Attorney, Agent, or Firm*—Morrison & Foerster

[57] ABSTRACT

This invention relates to an oil-in-water emulsion that is of a water-insoluble gas-forming chemical and a stabilizer. The emulsion being capable of forming microbubbles of gas upon application of ultrasonic energy. This composition allows for site specific imaging as the image enhancing microbubbles can be released upon the application of ultrasonic energy at the specific location where the image is desired.

13 Claims, 6 Drawing Sheets

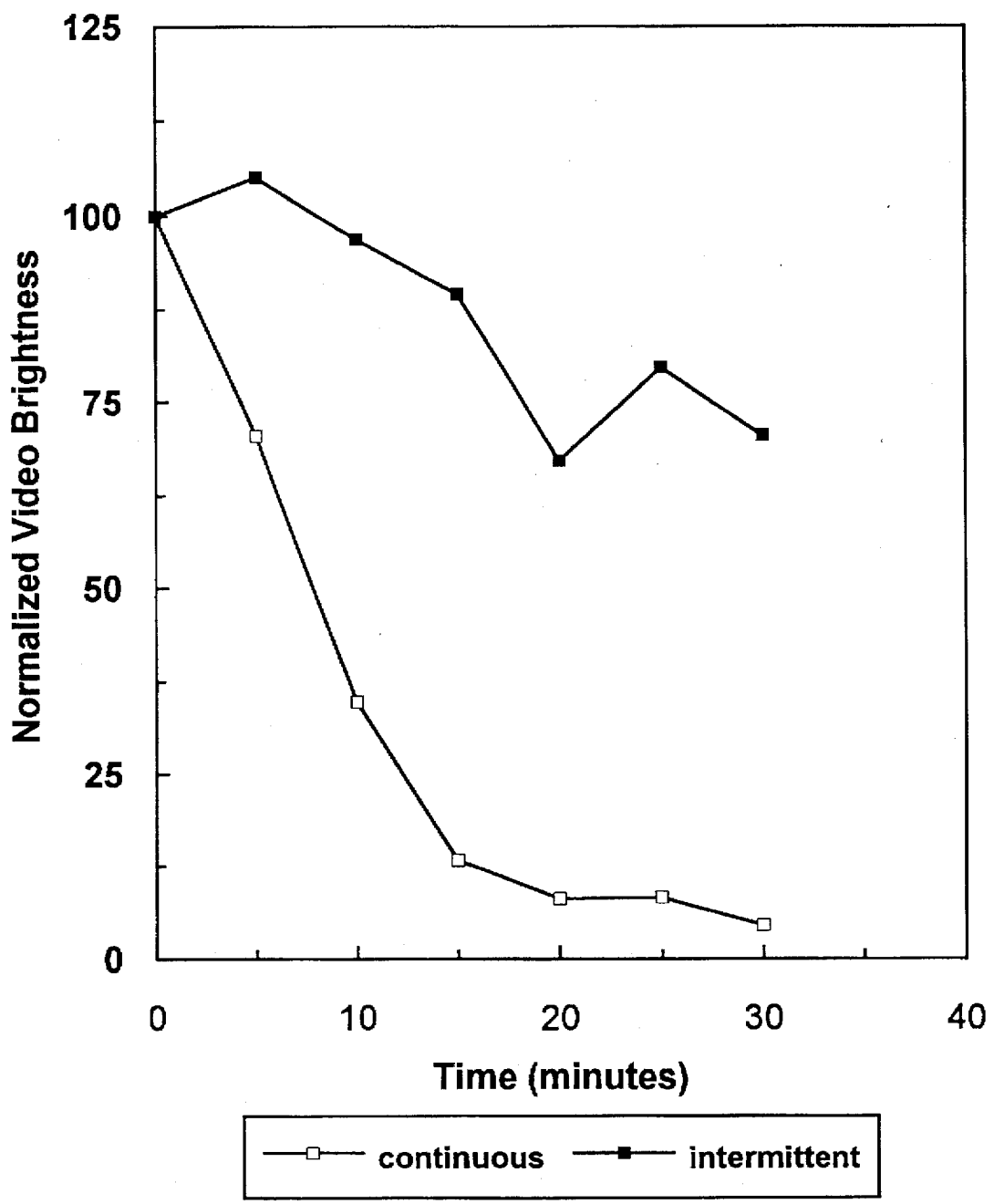

EMULSIONS AS CONTRAST AGENTS AND METHOD OF USE

BACKGROUND OF THE INVENTION

1. Field of the Invention

This invention relates to diagnostic ultrasonic imaging and contrast agents for use thereof. More particularly, it relates to ultrasonic contrast agents comprising emulsions capable of forming gas microbubbles upon the application of ultrasonic energy and methods for their use in diagnostic imaging.

2. Brief Description of the Background Art

Diagnostic ultrasonic imaging is based on the principal that waves of sound energy can be focused upon an area of interest and reflected in such a way as to produce an image thereof. The ultrasonic scanner utilized is placed on a body surface overlying the area to be imaged, and sound waves are directed toward that area. The scanner detects reflected sound waves and translates the data into images. When ultrasonic energy is transmitted through a substance, the amount of energy reflected depends upon the velocity of the transmission and the acoustic properties of the substance. Changes in the substance's acoustic properties (e.g. variations in acoustic impedance) are most prominent at the interfaces of different substances, such as liquid-solid or liquid-gas. Consequently, when ultrasonic energy is directed through media, changes in acoustic properties will result in more intense sound reflection signals for detection by the ultrasonic scanner.

Ultrasonic imaging agents of particular importance are composed of gas-containing substances which, when injected into the circulatory system, provide improved sound reflection and image clarity. One class of gas-containing imaging agents consists of microspheres of gas surrounded by a shell made of a biocompatible substance. These are best typified by ALBUNEX® (Molecular Biosystems, San Diego, Calif.: U.S. Pat. Nos. 4,572,203; 4,718,433; 4,744,958; 4,844,882 and 4,957,656) which consists of microspheres of air surrounded by albumin shells. Another such microspheric imaging agent is described by Holmes, et al. These microspheres consist of either non-proteinaceous crosslinked or polymerized amphipathic moieties forming micelles (PCT WO 92/17212) or crosslinked proteins (PCT WO 92/17213), both of which encapsulate gasses such as nitrogen, $SF_6$ and $CF_4$.

Another class of ultrasonic imaging agents can be described as microparticles of a solid or semi-solid substance containing gas which is entrapped in the microparticle matrix during production. Glajich, et al. (U.S. Pat. No. 5,147,631) describe the formation of porous particles of an inorganic material containing entrapped gas or liquid such as $O_2$, $CF_4$, perfluoroethane and argon. Erbel, et al. (U.S. Pat. No. 5,137,928) describe polyamino-dicarboxylic acid-co-imide derivatives capable of entrapping gasses such as air, argon and krypton. Albayrak, et al. (European Patent Specification 0 357 163) describe crystalline complexes entrapping gasses such as nitrogen, krypton, $SF_6$, cyclopropane and pentane which are dissolved in an aqueous vehicle such as protein or glycerol causing the release of gas bubbles. The aqueous vehicle, now containing a plurality of microbubbles of gas in solution, is then ready for use as an injectable ultrasonic imaging agent. Stein, et al. (European Patent Specification 327 490) describe microparticles containing amyloses or synthetic biodegradable polymers entrapping gasses or liquids with a boiling point less than 60° C.

Another class of gas-containing imaging agents are lipid vesicles or liposomes. Unger (U.S. Pat. Nos. 5,088,499 and 5,123,414) describes the encapsulation of gasses or gaseous precursors in liposomes, more particularly liposomes which contain ionophores for activation of gaseous precursors by way of a pH gradient. Henderson, et al. (PCT WO 92/15824) describe lipid vesicles with gas-filled center cores.

Still another class of imaging agents is composed of microbubbles of gas in solution. For example, Tickner, et al. (U.S. Pat. No. 4,276,885) describe microbubbles dispersed in liquified gelatin. More recently, Quay (PCT WO 93/05819) describes ultrasound imaging agents comprising microbubbles of selected gasses in solution. In a specific embodiment, Quay describes the formation of a gas-liquid emulsion of decafluorobutane. Also disclosed therein are imaging agents comprising aqueous dispersion of biocompatible gasses, some of which are gaseous at ambient temperature and others of which become gaseous at the body temperature of the subject being imaged.

The efficiency of gas as an ultrasound imaging agent is described by J. Ophir and K. J. Parker, *Contrast Agents in Diagnostic Ultrasound*, Ultrasound in Medicine and Biology (1989), Vol. 15(4) p. 319–333. However, the disadvantages of using gas as an ultrasound imaging agent have been and continue to be lacking of sufficient persistence of the gas in-vivo and in-vitro, and toxicity due to the introduction of gas into the venous system.

The present invention relates to site specific oil-in-water emulsions and is based on the unexpected observation that emulsions of gas-forming chemicals can be stabilized in the liquid state and will produce microbubbles when subjected to ultrasonic energy. The advantages are that such emulsions are more stable than most of the gas-containing imaging agents heretofor described, and their ability to form microbubbles when subjected to ultrasonic energy makes them site-specific and inherently less toxic due to less overall gas being introduced into the venous system.

SUMMARY OF THE INVENTION

This invention provides an emulsion which can be used as an ultrasonic imaging agent. The emulsion is made of at least one water-insoluble gas forming chemical and at least one stabilizer. This emulsion is capable of forming microbubbles of gas upon application of ultrasonic energy. The stabilizer is either a hydrophobic or amphipathic compound having a boiling point higher than that of the gas-forming chemical and, when present in the emulsion with the gas-forming chemical, acts as a stabilizer (maintains the gas-forming chemical in the liquid state) until the application of ultrasonic energy. The stabilizer causes the effective boiling point of the gas-forming chemical to be raised thereby preventing the volatilization of the gas-forming chemical until, it reaches a temperature above its boiling point at atmospheric pressure (760 mm). In this way, upon application of ultrasonic energy, the emulsified chemical becomes volatilized and produces gas microbubbles. In a specific embodiment the water-insoluble gas forming chemical is perfluoropentane and the stabilizer is lecithin. This invention also provides additional means to stabilize the emulsion for delivery to a patient. These means include delivery vehicles such as a natural polymer matrix, a synthetic polymer matrix or a liposome. More specifically, it is provided that the natural polymer matrix is an albumin matrix. This albumin matrix can be derivatized to contain polyethylene glycol.

This invention also provides a method to enhance the contrast of tissues and organs in an ultrasonic image comprising: (a) injecting at least one stabilized water insoluble gas forming chemical into a patient (b) applying a sufficient amount of ultrasonic energy to volatilize said chemicals to release microbubbles; and (c) detecting an ultrasonic image. The water insoluble gas forming chemical is stabilized with a hydrophobic or amphipathic stabilizer.

BRIEF DESCRIPTION OF THE DRAWINGS

FIG. 2 shows the difference in video brightness observed when the emulsion of Example 5 is either continually exposed to ultrasonic energy, or exposed only during 30 second intervals every 5 minutes.

DETAILED DESCRIPTION OF THE INVENTION

Figure 1A:
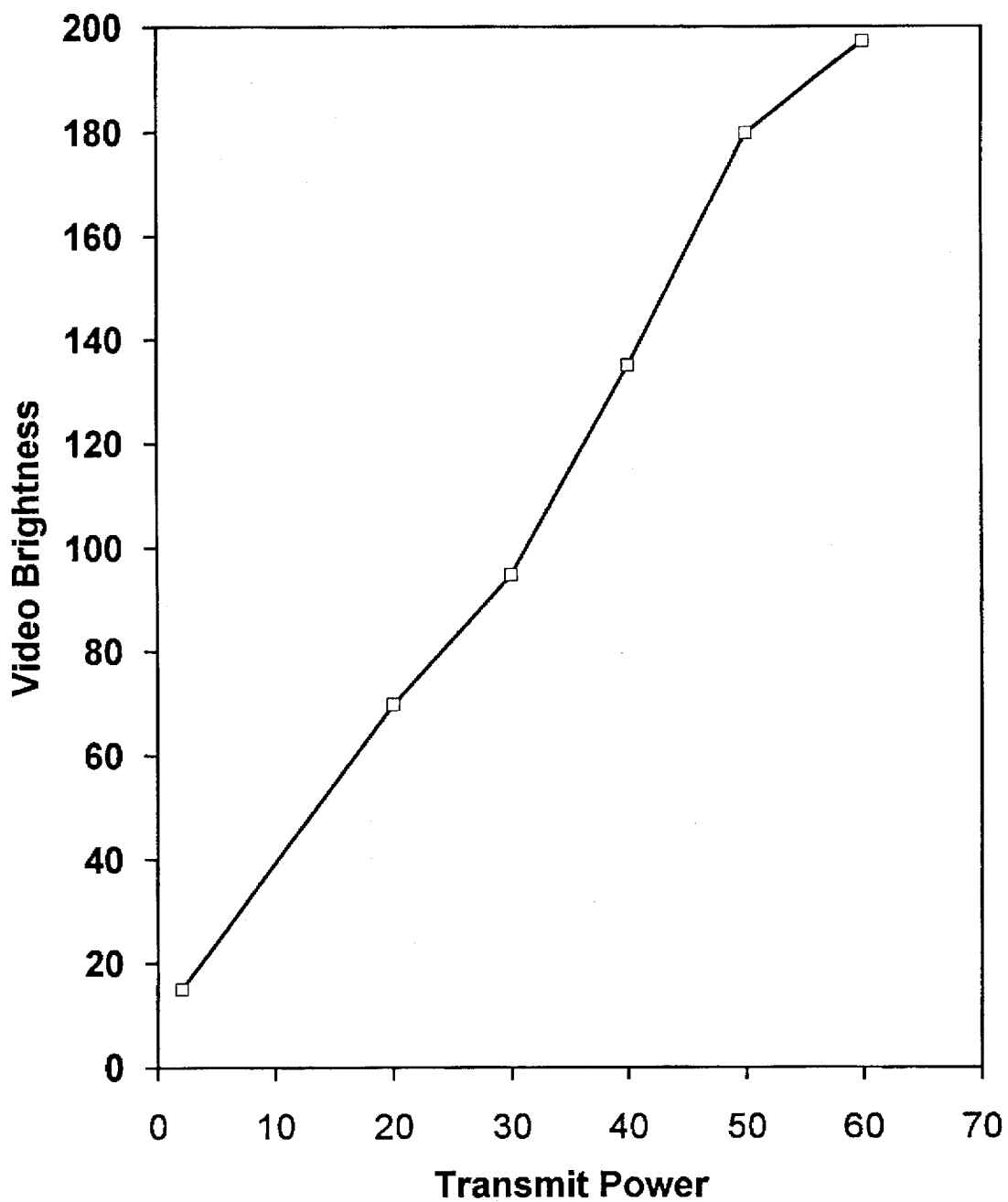
FIG. 1A shows the effects of increasing ultrasonic energy transmit power on reflectivity of the ultrasonic signal (expressed as video brightness) in the presence of an ALBUNEX® (Molecular Biosystems, San Diego, Calif.) sample.

We have now found that particularly effective site-specific ultrasonic contrast agents may be obtained by preparing emulsions of water-insoluble gas-forming chemicals. These gas-forming chemicals are stabilized by emulsification with a stabilizer. Additionally, the emulsification of the gas-forming chemicals, which are for the most part insoluble in water, serves to make the contrast agent more soluble and thus administrable to a patient. The water-insoluble gas-forming chemical must be capable of forming gas at the body temperature of the animal being imaged and will generally have a boiling point below body temperature. As discussed herein, boiling point will refer to the temperature at which the thermal energy of the molecules of a chemical are great enough to overcome the cohesive forces that hold them together in a liquid state (or solid state for chemicals which sublime and thus have no liquid state) at atmospheric pressure (760 nm). A stabilizer having a boiling point higher than that of the gas-forming chemical is necessary to stabilize the gas-forming chemical in the liquid state until the application of ultrasonic energy. The stabilizer causes the temperature at which the gas-forming chemical volatilizes to a gas to be raised to a temperature above its boiling point. In this way, the gas-forming chemical is actually both stabilized (maintained in a liquid state above its boiling point) and destabilized (capable of being volatilized upon exposure to ultrasonic energy) simultaneously. When the emulsion of the present invention is volatilized by exposure to ultrasonic energy, such as 50% transmit power at 5.0 MHz, gas microbubbles are formed and released from the emulsion thereby increasing the ultrasonic reflectivity in the area being imaged.

The water-insoluble gas-forming chemicals useful in the present invention can be further characterized as being non-toxic, physiologically compatible and generally having a boiling point below 37° C., and preferably between 26° C. and 34° C. Some of the gas-forming chemicals which would be useful in the present invention and their boiling points at atmospheric pressure are:

TABLE 1

| Gas-forming Chemical | Boiling Point, °C. |
|---|---|
| pentane | 36 |
| 1-pentene | 30 |
| perfluoropentane | 29.5 |
| 2-methyl butane (isopentane) | 27.8 |
| tetramethylsilane | 26 |
| 2-bromo-1,1,1-trifluoroethane | 26 |
| dibromodifluoromethane | 25 |
| fluorotrichloromethane | 24 |
| 2 H-perfluoro-t-butane | 13 |
| cyclobutane | 12 |
| heptafluoropropylbromide | 12 |
| 1-chloro-1,1,2,2-tetrafluoroethane | 10.2 |
| neopentane | 9.5 |
| teflurane | 8 |
| 2-chloro-1,1,1-trifluoroethane | 6.9 |
| decafluorobutane | 4 |
| butane | −.5 |
| 2-chloro-1,1,1,2-tetrafluoroethane | −12 |
| 2 H-heptafluoropropane | −15 |
| iodotrifluoromethane | −22.5 |
| cyclopropane | −33 |
| perfluoroethylamine | −35 |
| octafluoropropane | −36 |
| $SF_6$ (sulfur hexafluoride) | −64 |

The stabilizer of the present invention may be a hydrophobic or amphipathic (containing both hydrophobic and hydrophilic entities) compound. Hydrophobic compounds include di- and triglycerides; saturated and unsaturated hydrocarbons; perfluorocarbons such as perfluorohexane or perfluorodecalin; fats and fatty oils such as triolein.

Amphipathic compounds include phospholipids such as, phosphatidic acid, phosphatidylglycerol, and phosphatidylinositol; alkali salts of fatty acids; ionic surfactants such as sodium dodecyl sulfate; non-ionic surfactants such as PLURONIC® F-68 (trade name for poloxamer 188, a block copolymer of polyoxyethylene and polyoxypropylene (CAS-9003-11-6)

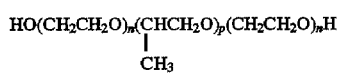

wherein the average value of n=75 and the average value of p=30 such that the average molecular weight of said compound is 8350) and polysorbate 80; zwitterionic surfactants such as phosphatidylcholine (lecithin), phospatidylethanolamine and phosphatidylserine; amino acid polymers or proteins with hydrophilic and hydrophobic moieties such as albumin.

Amphipathic compounds which are particularly useful as stabilizers of fluorinated gas-forming compounds are themselves fluorinated. These compounds act as both stabilizers and solubilizers of fluorinated gas-forming compounds, due to the fluorine-fluorine interactions between the two compounds. Such fluorinated stabilizers generally have a hydrophobic fluorocarbon chain connected to a hydrophilic moiety, such as a polyether, sugar, carboxylate, sulfonate or a quaternary ammonium group. Examples of fluorinated stabilizers can be found in U.S. Pat. Nos. 5,077,036, 5,080, 855 and 4,987,154, each of which is incorporated herein by reference.

When the boiling point of the gas-forming chemical is below the temperature at which the emulsion is prepared and stored, such as less than 24° C., it is still possible to form a liquid-liquid oil-in-water emulsion of the present invention by using a stabilizer which is capable of strong hydrophobic interations with the gas-forming chemical which will maintain the gas-forming chemical in a liquid state above its boiling point. Particularly useful stabilizers for this purpose are C5 to C20 perfluorocarbons or hydrocarbons and can be either hydrophobic or amphipathic.

The stabilizer may be used singly or in various combinations in the emulsions of the present invention. However, when the stabilizer is a hydrophobic compound, it will be necessary to also have present a surface active agent either within the emulsion or in association with the emulsion in order for the emulsion to be soluble and thus physiologically tolerated. Surface active agents, or surfactants, are characterized as being substances that lower the surface tension between two liquids. A surface active agent will generally be an amphipathic compound as described above or may also be a cationic or anionic compound. Additionally, a surfactant and a co-surfactant combination, such as phosphatidylcholine and PLURONIC® F-68 is also contemplated.

When the stabilizer is amphipathic, the presence of an additional hydrophobic compound is generally not necessary. In particular, the chemical PLURONIC® F-68 has been found to sufficiently solubilize and stabilize the gas-forming chemical in the absence of an additional hydrophobic compound.

The amount of stabilizer present in the emulsion of the present invention will vary over a wide range of concentrations depending on the concentration and properties of the other components of the emulsion and will be principally dependent on the amount and characteristics of the gas-forming chemical. This is exemplified in the example section.

Optionally present in the emulsion are viscosifiers which are generally polyalcohols or carbohydrates such as glycerol, sorbitol, lactose, sucrose and dextrans, and preferably glycerol at a concentration between 5–15% (w/v). Other optional constituents are anti-oxidants such as α-tocopherol, preferably at a concentration of 0.1 to 0.25% (w/v). Still another class of optional components are compounds which impart organ or tissue target specificity to the emulsion. These compounds may include steroids such as cholesterol, proteins, lipoproteins and antibodies.

The emulsion of the present invention may be useful as an ultrasonic imaging agent either by itself or in combination with a delivery vehicle which may be used to impart greater stability, both in-vivo and in-vitro, or tissue or organ target specificity. One such delivery vehicle can be made from a natural polymer which forms a matrix, such as an albumin matrix, with multiple chambers which contain the emulsion of a gas-forming chemical. The surface of the albumin matrix so described may also be modified to contain a polymer such as polyethylene glycol to reduce reticular endothelial system uptake in vivo.

Further examples of delivery vehicles comprise the use of synthetic polymers, such as the polyamino dicarboxylic acid-co-imide derivatives disclosed in U.S. Pat. No. 5,190,982 incorporated herein by reference or the crosslinkable synthetic polymers such as polyphosphazines described in U.S. Pat. No. 5,149,543 incorporated herein by reference. Another delivery vehicle may comprise a liposome. In addition to the delivery vehicles described, it is understood that any delivery vehicle designed to make hydrophobic compounds, whether they are therapeutic or diagnostic compounds, administrable to a patient is also contemplated.

The emulsions of the present invention, whether or not they are incorporated into a delivery vehicle will generally have a size below 8.0μ, and preferably below 5.0μ. It is additionally anticipated that microemulsions can be prepared according to the present invention with a size below 1.0μ.

EXAMPLE 1

An emulsion useful for stabilizing the gas-forming chemical was made by mixing the following components together by rotating under vacuum.

| | |
|---|---|
| Glycerol Trioleate (triolein) | 1.25 g |
| 1,2-dioleoyl-glycero-3-phosphocholine (20 mg/ml in chloroform) | 15 ml |
| cholesterol | 0.05 g |
| α-tocopherol | 0.012 g |

Any remaining solvent was removed by drying under high vacuum at room temperature (20°–25° C.). After 16 hours, 1.58 g of glycerol (1.26 g/ml) and 0.2 g perfluoropentane were added. Then, 9.6 ml of water were added slowly while mixing at 10,000 rpm in a POLYTRON® PT3000 (Brinkman, Westbury, N.Y.) for 2 minutes at 0° C. The resultant emulsion was further homogenized for 3 minutes at 30,000 rpm.

EXAMPLE 2

The ultrasonic imaging characteristics of the emulsion of Example 1 were studied using an HP SONOS 100 Ultrasound Imaging system (Hewlett-Packard, Palo Alto, Calif.) with a 5 MHz transducer (focal zone=3.5 cm) in sector mode to detect the scattering capability of the sample solution. The compression was adjusted to obtain the greatest dynamic range possible, i.e. 60 dB. The time gain compensation control of the ultrasound system was adjusted until the image sector being imaged is judged visually to be optimal.

The imaging sequence was started by optimizing the instrument as described on 1.0 L of water at 37° C. at 2% transmit power. A 1.0 ml sample was then injected into the water. Thereafter, every 2 minutes the transmit power was adjusted upwards to 10, 20, 30, 40, 50, 60, 70, 80, 90 and 99%. The entire sequence of images was recorded on videotape (attached to the ultrasound system) for storage and analysis.

To prepare quantitative results of this experiment, videodensitometry analysis was performed. Selected video frames stored on the videotape were digitized using an Apple Macintosh II computer equipped with a Data Translation QuickCapture frame grabber board. These frames were analyzed using CineProbe® version 1.0 (Molecular Biosystems, San Diego, Calif.) image processing software. A Region of Interest (ROI) within the beaker was selected and the mean pixel intensity (video brightness) within the region was determined. Each frame was then analyzed as to its mean videodensity within the region of interest. The videodensity of a water blank is subtracted and the resultant videodensity is expressed as Video Brightness or Normalized Video Brightness when the initial value is set to 100 for comparison.

An ALBUNEX® (Molecular Biosystems, San Diego, Calif.) (microbubbles surrounded by a protein shell prepared as described in U.S. Pat. Nos. 4,572,203; 4,718,433; 4,744,958; 4,844,882 and 4,957,656) control was also prepared and analyzed as described by injecting a 1.0 mL sample of ALBUNEX® (Molecular Biosystems, San Diego, Calif.) into 1.0 Liter of 37° water.

Figure 1B:
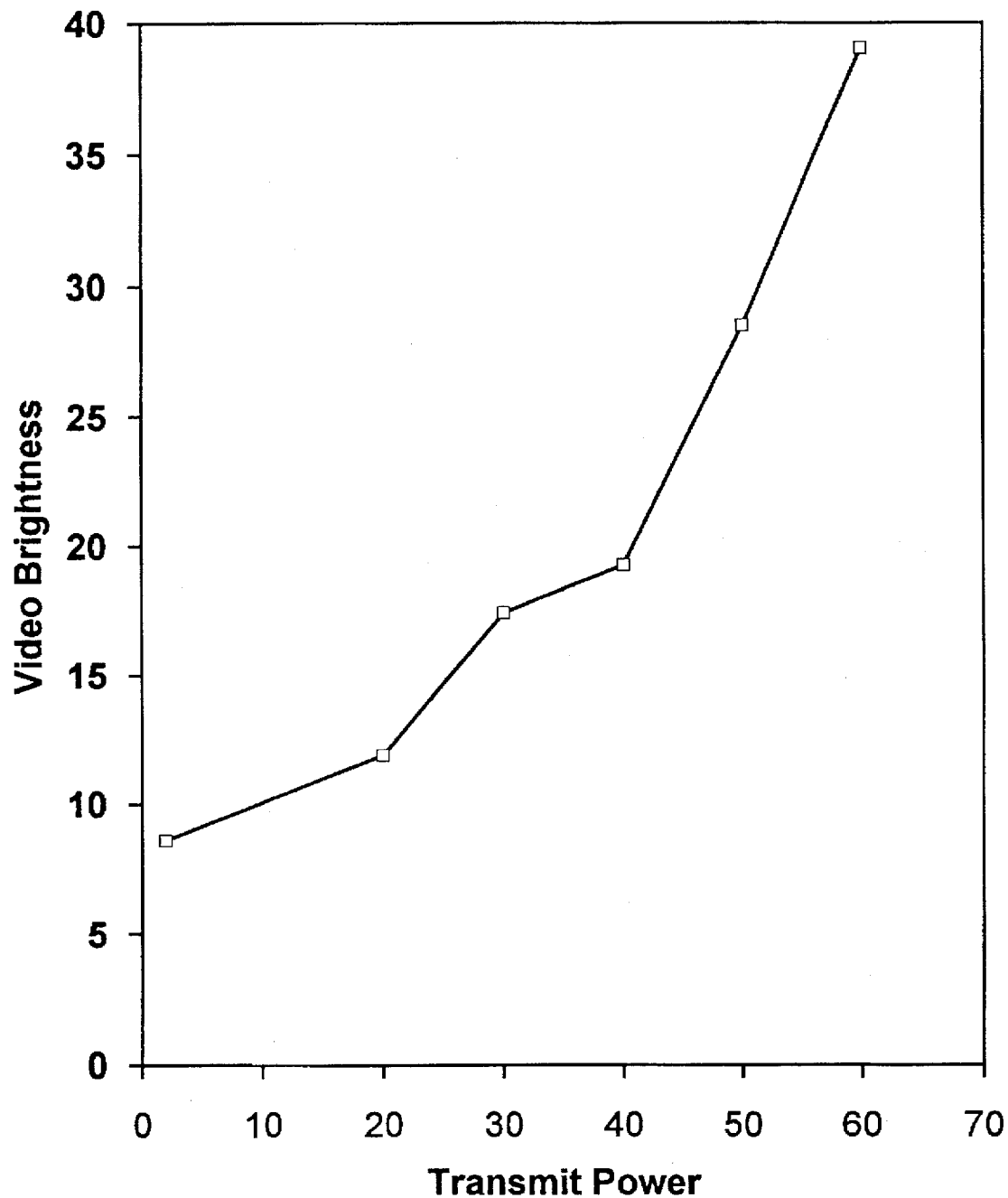
FIG. 1B shows the effects as described in FIG. 1A in the presence of the perfluoropentane emulsion of Example 1.

The results of this experiment are depicted in FIG. 1A and 1B. Due to the unchanging number of microbubbles present in the ALBUNEX® (Molecular Biosystems, San Diego, Calif.) sample, there would be expected to be a linear relationship between transmit power and video brightness.

This linear relationship is depicted in FIG. 1A. In comparison, using the emulsion of Example 1, there would be the expectation of a bilinear or step function between video brightness and transmit power which would be due to some threshold energy of cavitation for microbubbles to be formed upon exposure to ultrasonic energy. Such a relationship was observed, and these results are depicted in FIG. 1B.

EXAMPLE 3

The following components were added together and homogenized in the POLYTRON® (Brinkman, Westbury, N.Y.) at 0° C. for 3 minutes at 10,000 rpm while slowly adding 10 ml ultrapure water:

| Triolein | 0.6 g |
|---|---|
| Glycerol | 1.57 g |
| Lecithin | 0.6 g |
| Perfluoropentane | 1.5 g |

These components were further homogenized for an additional 2 minutes at 30,000 rpm to produce a milky white emulsion. This emulsion was filtered successively through a 5μ and 1.2μ filter. The particle size was determined in a Nicomp 770 (Particle Sizing Systems, Santa Barbara, Calif.) to be 95% less than 3.8μ. It was stable (no appreciable phase separation or particle size increase) for several days at 4° C. When imaged as described in Example 2, this emulsion demonstrated microbubble formation above 40% transmit power as observed in the ultrasonic image.

EXAMPLE 4

The following components were added together and homogenized in the POLYTRON (Brinkman, Westbury, N.Y.) at 0° C. for 3 minutes at 10,000 while slowly adding 20 ml water:

| Triolein | 1.0 g |
|---|---|
| Glycerol | 1.0 g |
| α-Tocopherol | 0.02 g |
| PLURONIC ® F-68 | 0.2 g |
| Gas-forming Chemical | 1.5 g of one of the following: |
| Emulsion A: | FCCl$_3$ (Fluorotrichloromethane) |
| Emulsion B: | Br$_2$F$_2$C (Dibromodifluoromethane) |
| Emulsion C: | TMS (Tetramethylsilane) |
| Emulsion D: | 2-Methyl butane (Isopentane) |

The above emulsions were filtered through a 1.2μ filter and the particle sizes were determined as described in Example 4 to be:

| A | 95% less than 2.97 μ |
|---|---|
| B | 95% less than 4.02 μ |
| C | 95% less than 2.18 μ |
| D | 95% less than 2.99 μ |

EXAMPLE 5

The following components were added together and homogenized in the POLYTRON® (Brinkman, Westbury, N.Y.) at 0° C. for 5 minutes at 10,000 rpm while slowly adding 20 ml water:

| Triolein | 1.0 g |
|---|---|
| Glycerol | 3.0 g |
| α-Tocopherol | 0.02 g |
| Lecithin | 1.0 g |
| Perfluoropentane | 1.0 g |

The emulsions were further homogenized for 3 minutes at 20,000 rpm and filtered successively through a 5μ and 1.2μ filter. The ultrasonic imaging characteristics of the emulsion was studied as described in Example 2 and exhibited microbubble formation above 40% transmit power as observed in the ultrasonic image.

EXAMPLE 6

To further study the effects of ultrasonic energy on the production of microbubbles, the emulsion of Example 5 (perfluoropentane) was imaged in two separate experiments either continually or in 30 second intervals. For each experiment, a 1.0 ml sample of the emulsion was added to 1.0 liter of water at 37° C. In the first experiment, ultrasonic imaging as described in Example 2 was carried out at 99% transmit power continuously for 30 minutes. In the second experiment, the ultrasonic imaging was carried out for 30 second durations once every 5 minutes (intermittent imaging). Image brightness was quantified as described in Example 2 and the results are depicted in FIG. 2. These results demonstrate that with continuous ultrasonic energy, due to the constant production of microbubbles and depletion of the bubble-forming capability of the emulsion, image brightness was significantly diminished at the end of 30 minutes. In comparison, with intermittent imaging which exposed the emulsions to only one tenth the energy as compared to constant imaging (30 seconds every 5 minutes), the microbubble-forming capability of the emulsion persisted and a substantial amount of microbubbles continued to be produced even after 30 minutes.

EXAMPLE 7

An alternative emulsion formulation comprises a viscosifier, a stabilizer which is amphipathic and a gas-forming chemical formed by mixing together the following components in a final volume of 50 mL water:

|  | Viscosifier: | Stabilizer: |
|---|---|---|
| Emulsion A | PLURONIC ® F-68 (0.5 g) | Sucrose (8.6 g) |
| Emulsion B | Sodium dodecyl-sulfate (1.44 g) | Sucrose (8.6 g) |
| Emulsion C | PLURONIC ®F-68 (0.5 g) | Lactose (9.0 g) |
| Emulsion D | Sodium dodecyl-sulfate (1.44 g) | Lactose (9.0 g) |

The solutions from above were filtered through a 0.2μ filter. A 10 mL aliquot of each of the above were mixed with 0.168 mL of perfluoropentane in the POLYTRON® (Brinkman, Westbury, N.Y.) at 0° C. for 1 to 3 minutes at 10,000 to 20,000 rpm and then for an additional 5 minutes at 20,000 rpm. Each of these four emulsions demonstrated microbubble formation as observed in the ultrasonic image above 40% transmit power when studied as described in Example 2.

Figure 3:
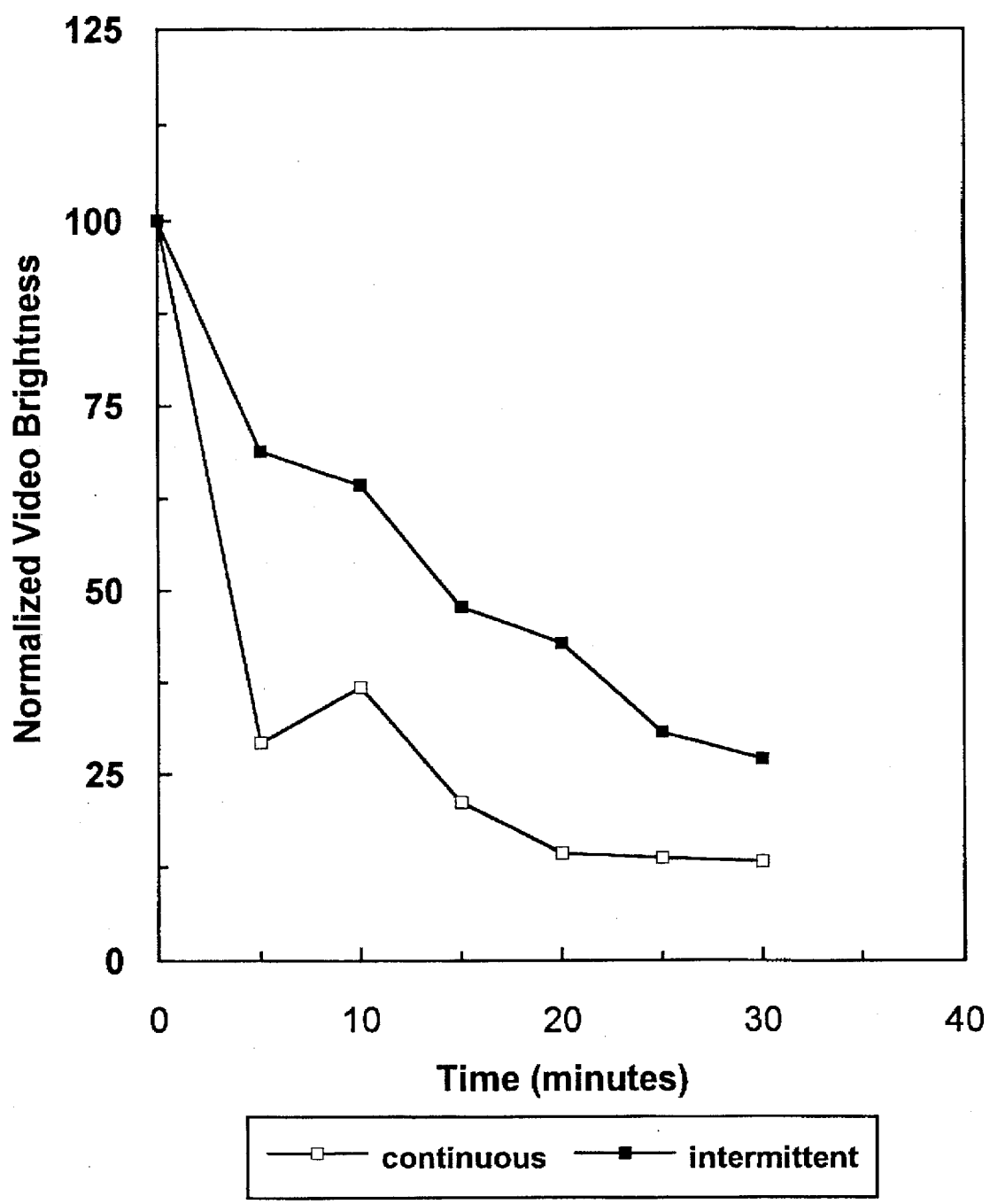
FIG. 3 shows the difference in video brightness observed when Emulsion C of Example 7 is either continually exposed to ultrasonic energy, or exposed only during 30 second intervals every 5 minutes.

To study the effects on these emulsions of continuous verses intermittent exposure to ultrasonic energy, a 1.0 mL sample of Emulsion C was placed in 1.0 liter of degassed water at 37° C. This solution was ultrasonically imaged either continuously or in intervals as described in Example 6. The results are depicted in FIG. 3.

EXAMPLE 8

SYNTHESIS OF NONAFLUORO-t-BUTYLMETHANE $C_4F_9CH_3$

Starting materials (methyl iodide and cesium fluoride) were obtained from Aldrich Chemical Company and perfluoroisobutylene gas was obtained from Flura Corporation. Nuclear magnetic resonance spectra were obtained using a 200 MHz instrument tuned for determination of proton ($^1H$) or fluorine ($^{19}gF$) resonances.

Figure 4:
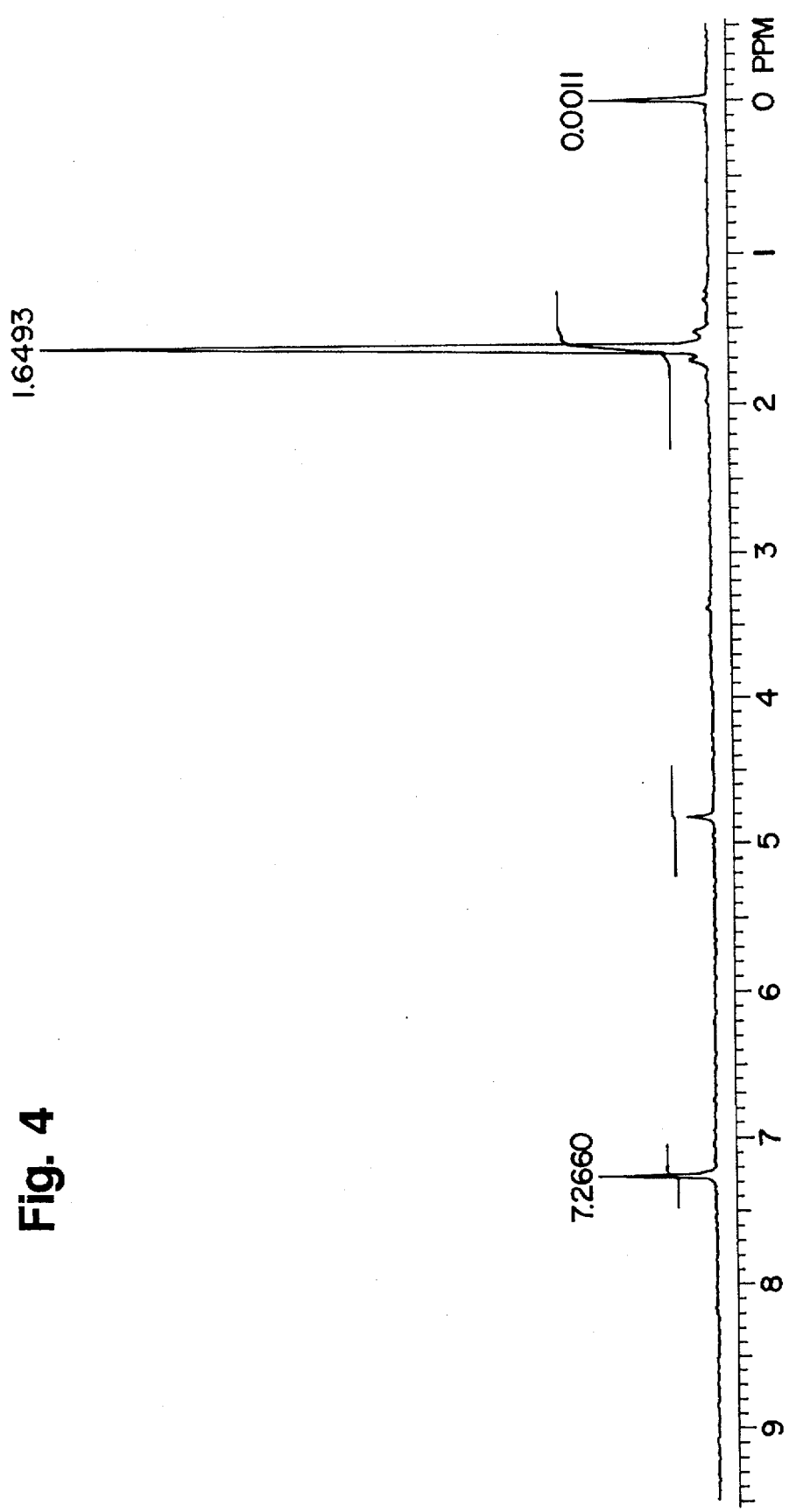
FIG. 4 shows the $^1$HNMR spectrum of a $CDCl_3$ solution of nonafluoro-t-butylmethane ($C_4F_9CH_3$).
Figure 5:
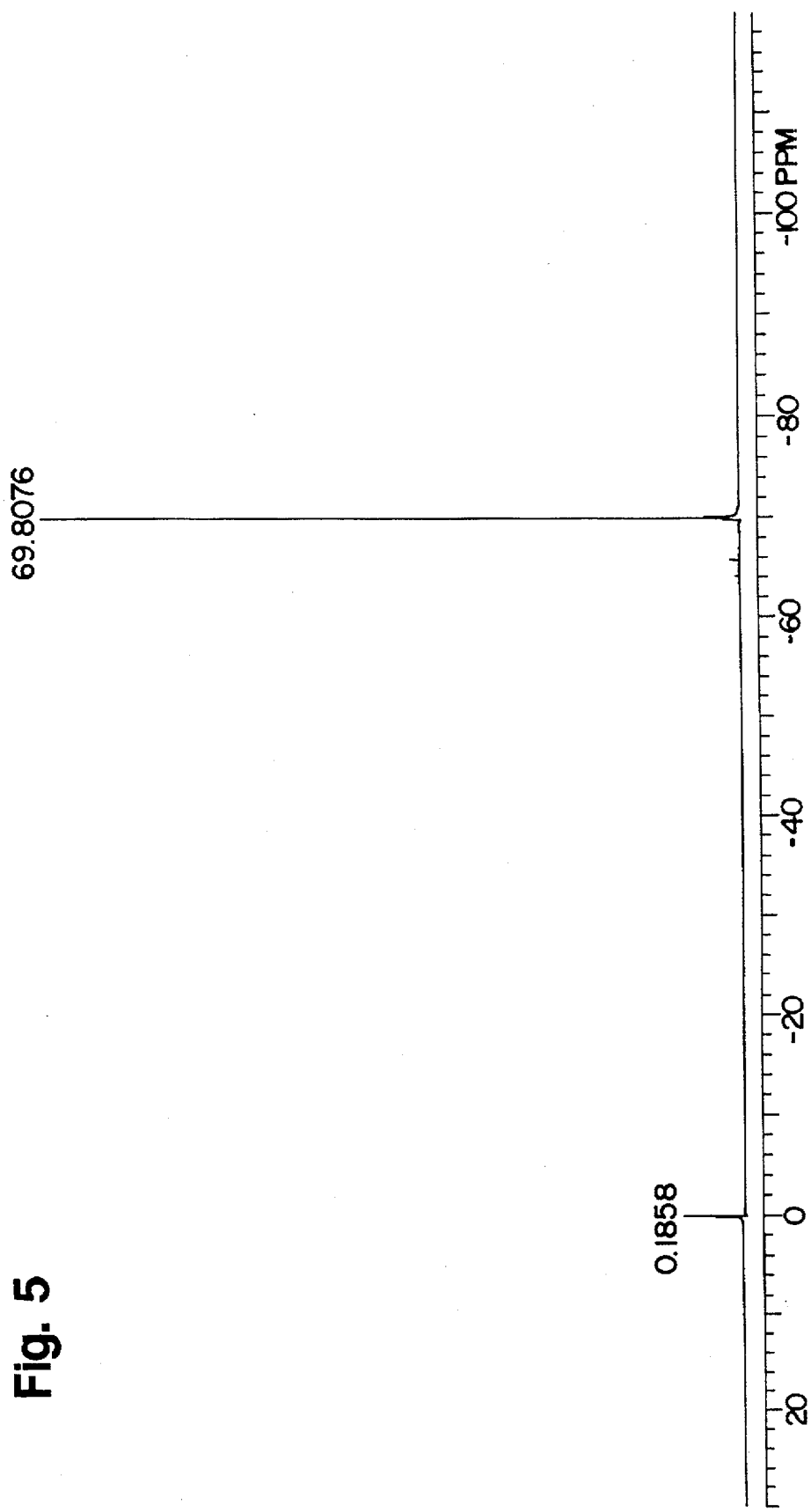
FIG. 5 shows the $^{19}$F NMR spectrum of a $CDCl_3$ solution of nonafluoro-t-butylmethane ($C_4F_9CH_3$).

In a flask equipped with a gas inlet, mechanical stirrer and a dry ice condenser was placed a suspension of dry cesium fluoride (42.5 g, 0.279 mol) in diglyme (200 mL). Perfluoroisobutylene gas (55.5 g, 0.278 mol) was bubbled in. The gas reacted rapidly with cesium fluoride and a yellow solution resulted. The mixture was stirred for 30 minutes and then methyl iodide (38.5 g, 0.271 mol) was added dropwise. The reaction was slightly exothermic and the cesium iodide separated out. The mixture was stirred for 3 hours and was allowed to stand overnight. A cold solution (2M, sodium chloride, 500 mL) was added to the mixture with cooling (5° C.) for 30 minutes. Sodium iodide and most of the diglyme solvent dissolved in the aqueous phase which was then decanted off from the solid giving a crude yield of 45 g ($\equiv$40%). Distillation of the compound sublimed at head temperature 35°–39° C. and bath temperature not exceeding 50°–55° C. The product was collected in a receiver cooled to –30° C. with dry ice and ethanol. The proton $^1H$ NMR spectrum of its $CDCl_3$ solution showed a single resonance relative to TMS; 1.65 (s, 3H, $CH_3$) ppm (see FIG. 4) and the $^{19}F$ spectrum, in the same solvent showed also one single resonance at –69.99 (s, 9F) ppm relative to $CDCl_3$ (see FIG. 5).

NONAFLUORO-t-BUTYLMETHANE $C_4F_9CH_3$ is shown according to either of the following chemical formulas:

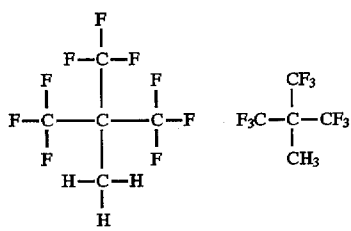

EXAMPLE 9

The following components were mixed together and homogenized in the POLYTRON® (Brinkman, Westbury, N.Y.) at 0° C. for 3 minutes at 10,000 rpm while slowly adding 10 mL ultra pure water.

| Triolein | 1.01 g |
|---|---|
| Glycerol | 1.05 g |
| α-Tocopherol | 0.02 g |
| PLURONIC ® F-68 | 0.099 g |
| $C_4F_9CH_3$ | 0.780 g |

The resultant emulsion was filtered through a 5µ filter. The particle size was determined as described in Example 4 to be less than 4.30 microns.

The ultrasonic imaging characteristics of the emulsion were studied as described in Example 2. The formation of gas bubbles was observed even at low transmit power (<25%) settings which became brighter as the transmit power was slowly increased to 99%.

Also for comparison a control experiment without $C_4F_9CH_3$ was conducted by mixing the following components:

| Triolein | 1.01 g |
|---|---|
| Glycerol | 1.05 g |
| α-Tocopherol | 0.021 g |
| PLURONIC ®-F68 | 0.204 g |

The emulsion was prepared as described above. In contrast to the previous ultrasound imaging experiment, microbubble formation was not observed even at 99% transmit power.

EXAMPLE 10

The following components were added together and homogenized in the POLYTRON® (Brinkman, Westbury, N.Y.) at 0° C. for 2 minutes at 10,000 rpm while slowly adding 10 ml water:

| Triolein | 1.0 g |
|---|---|
| Glycerol | 1.0 g |
| α-Tocopherol | 0.03 g |
| PLURONIC ® F-68 | 0.1 g |
| Isopentane | 0.15 g |
| n-Pentane | 0.85 g |

The emulsion was further homogenized for 6 minutes at 30,000 rpm and filtered through a 1.2µ filter. The ultrasonic imaging characteristics of the emulsion was studied as described in Example 6 and a higher level of video brightness was observed with intermittent imaging than with continuous imaging.

EXAMPLE 11

EMULSION-CONTAINING ALBUMIN MICROPARTICLE

The emulsion of the present invention can be encapsulated into a delivery vehicle comprising a multi-chamber albumin matrix as follows:

A primary emulsion is prepared by first dissolving 2.0 g human serum albumin in 20.0 ml buffer (0.45N $Na_2CO_3$, pH 9.8) and then adding 1.0 g perfluoropentane. This mixture is emulsified in an osterizer at high speed for 10 minutes.

A double emulsion is then prepared by adding 100 ml Chloroform:Cyclohexane (1:4 v/v) with 10% (v/v) sorbitan trioleate with continued mixing for 10 minutes.

The albumin is cross-linked by adding, while continuing to mix, an additional 100 ml Chloroform:Cyclohexane (1:4 v/v) containing 2.5 g terephthaloyl chloride and continuing to mix for an additional 30 minutes. The reaction is quenched with 100 mL of cyclohexane containing 5g% polysorbate and 10% (v/v) ethanolamine. The microcapsules are washed 3 times with cyclohexane:ethanol (1:1 v/v), followed by 2 washes in 5% polysorbate-95% ethanol, 2 washes in 95% ethanol and 2 washes in water. The microparticles are then resuspended in normal saline and comprise multi-chambered vesicles containing an inner emulsified matrix of perfluoropentane.

Although the invention has been described primarily in connection with special and preferred embodiments, it will be understood that it is capable of modification without departing from the scope of the invention. The following claims are intended to cover all variations, uses, or adaptations of the invention, following in general, the principles thereof and including such departures from the present disclosure as come within known or customary practice in the field to which the invention pertains, or as are obvious to persons skilled in the art.

What is claimed is:

1. A site-specific liquid-liquid emulsion useful as an imaging agent for ultrasonic imaging of an animal, comprising:

(a) water;
   (b) at least one water-insoluble gas-forming biocompatable chemical having a boiling point below 37° C., wherein the chemical in said emulsion is in the liquid state at 37° C. and at atmospheric pressure in the absence of exposure to ultrasonic energy and is present in said emulsion in an amount sufficient to form microbubbles upon exposure to ultrasonic energy; and
   (c) at least one stabilizer comprising a hydrophobic or amphipathic compound in an amount sufficient to keep the gas-forming chemical in the liquid state at 37° C., at atmospheric pressure, and prior to exposure to ultrasonic energy.

2. The emulsion of claim 1 wherein said stabilizer is a hydrophobic compound.

3. The composition of claim 2 wherein said emulsion includes a surface active agent.

4. The emulsion of claim 1 wherein said stabilizer is amphipathic.

5. The emulsion of claim 4 wherein said amphipathic compound is:

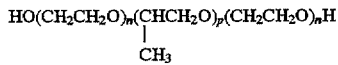

wherein the average value of n=75 and the average value of p=30 such that the average molecular weight of said compound is 8350.

6. The composition of claim 1 wherein said emulsion includes a viscosifier.

7. The composition of claim 1 wherein said emulsion includes antioxidants.

8. An ultrasound imaging agent comprising the emulsion of claim 1 and a delivery vehicle.

9. The ultrasound imaging agent of claim 8 wherein said delivery vehicle is selected from the group consisting of: a natural polymer matrix, a synthetic polymer matrix or a liposome.

10. The ultrasound imaging agent of claim 9 wherein said natural polymer matrix is an albumin matrix.

11. The emulsion of claim 1 wherein said water-insoluble gas-forming chemical is nonafluoro-t-butylmethane.

12. The emulsion of claim 1 wherein said water-insoluble gas forming chemical is perfluoropentane and said stabilizer is lecithin.

13. A site-specific liquid-liquid emulsion useful as an imaging agent for ultrasonic imaging of an animal, comprising:

(a) water;
   (b) at least one perfluorocarbon having a boiling point below 37° C., wherein the perfluorocarbon in said emulsion is in the liquid state at 37° C. and at atmospheric pressure in the absence of exposure to ultrasonic energy and is present in said emulsion in an amount sufficient to form microbubbles upon exposure to ultrasonic energy; and
   (c) at least one stabilizer comprising a hydrophobic or amphipathic compound in an amount sufficient to keep the perfluorocarbon in the liquid state at 37° C., at atmospheric pressure, and prior to exposure to ultrasonic energy.

* * * * *